(12) United States Patent
Sekine et al.

(10) Patent No.: US 9,289,454 B2
(45) Date of Patent: Mar. 22, 2016

(54) METHOD FOR MANUFACTURING MULTILAYERED CELL SHEET, MULTILAYERED CELL SHEET HAVING VASCULAR NETWORK OBTAINED THEREBY, AND METHOD OF USE THEREOF

(75) Inventors: Hidekazu Sekine, Shinjuku-ku Tokyo (JP); Tatsuya Shimizu, Shinjuku-ku Tokyo (JP); Teruo Okano, Shinjuku-ku Tokyo (JP)

(73) Assignee: Tokyo Women's Medical University, Tokyo (JP)

( * ) Notice: Subject to any disclaimer, the term of this patent is extended or adjusted under 35 U.S.C. 154(b) by 0 days.

(21) Appl. No.: 13/822,945

(22) PCT Filed: Sep. 14, 2011

(86) PCT No.: PCT/JP2011/071055
§ 371 (c)(1),
(2), (4) Date: Mar. 13, 2013

(87) PCT Pub. No.: WO2012/036224
PCT Pub. Date: Mar. 22, 2012

(65) Prior Publication Data
US 2013/0171213 A1  Jul. 4, 2013

(30) Foreign Application Priority Data
Sep. 14, 2010  (JP) ................................. 2010-225200

(51) Int. Cl.
| A61K 35/44 | (2015.01) |
| A61K 35/34 | (2015.01) |
| A61K 35/36 | (2015.01) |
| C12N 5/077 | (2010.01) |
| A61L 27/36 | (2006.01) |
| A61L 27/38 | (2006.01) |

(52) U.S. Cl.
CPC ................. *A61K 35/44* (2013.01); *A61K 35/34* (2013.01); *A61K 35/36* (2013.01); *A61L 27/3604* (2013.01); *A61L 27/3839* (2013.01); *A61L 27/3895* (2013.01); *C12N 5/0657* (2013.01); *C12N 2502/28* (2013.01); *C12N 2513/00* (2013.01)

(58) Field of Classification Search
None
See application file for complete search history.

(56) References Cited

U.S. PATENT DOCUMENTS
2004/0009566 A1 *  1/2004  Okano et al. ............... 435/174
2008/0131476 A1 *  6/2008  Kanzaki et al. ............. 424/423

FOREIGN PATENT DOCUMENTS
| JP | 2009-531067 A | 9/2009 |
| WO | 02/08387 A | 1/2002 |
| WO | 02/078439 A2 | 10/2002 |
| WO | 2010/065957 A2 | 6/2010 |
| WO | 2010/065957 A3 | 6/2010 |

OTHER PUBLICATIONS

Sasagawa et al., Design of prevascularized three-dimensional cell-dense tissues using a cell sheet stacking manipulation technology, Biomaterials, 31, p. 1646-1654, 2010.*
Shimizu et al., Polysurgery of cell sheet grafts overcomes diffusion limits to produce thick, vascularized myocardial tissues, FASEB Journal, 2006.*
Sekine et al., Pulsatile Myocardial Tubes Fabricated with Cell Sheet Engineering, Circulation, 2006, 114:I-87-I-93.*
Sekine et al., Endothelial Cell Coculture Within Tissue-Engineered Cardiomyocyte Sheets Enhances Neovascularization and Improves Cardiac Function of Ischemic Hearts, Circulation, 2008, 118:S145-S152.*
EpigastricFlap, Anatomy of Caudal area, 2014.*
Koning et al., Current Opportunities and challenges in skeletal muscle tissue engineering, J. Tissue Eng. Regen. Med, 2009, 3:407-415.*
Tanaka et al., Tissue Engineering Skin Flaps, Experimental, 2002.*
Masuda et al., Cell Sheet engineering for heart tissue repair, Advanced Drug Delivery Reviews, 2008, 60:277-285.*
Matsuda et al, Tissue Engineering Based on Cell Sheet Technology, Advanced Materials, 2007, 19, 3089-3099.*
Todd et al., Hydration Forces, Wiley Encyclopedia of Chemical Biology, 2008.*
Lovett et al., Vascularization Strategies for Tissue Engineering, Tissue Engineering: Part B, vol. 15, No. 3, 2009.*
Bach et al., A new approach to tissue engineering of vascularized skeletal muscle, J. Cell. Mol. Med. vol. 10, No. 3, 2006 pp. 716-726.*
International Search Report corresponding to PCT/JP2011/071055 mailed Nov. 15, 2011, 4 pages.
International Search Report corresponding to PCT/JP2011/071056 mailed Dec. 20, 2011, 3 pages.

(Continued)

*Primary Examiner* — Renee Claytor
*Assistant Examiner* — Srikanth Patury
(74) *Attorney, Agent, or Firm* — Kilpatrick Townsend & Stockton LLP

(57) ABSTRACT

A method for producing multilayered cell sheets, including producing a vascular bed which includes an artery-vein loop and in which a capillary vascular network is constructed; layering cell sheets on the vascular bed; and perfusing a culture medium in vitro to construct a vascular network in the cell sheets. The production method enables vascular networks to be constructed in cell sheets and enables thick multilayered cell sheets to foe easily produced by layering the cell sheets. Such thick multilayered cell sheets are useful as in vivo tissue-like products for regenerative medicine for various tissues and for evaluation of drugs and the like.

9 Claims, 8 Drawing Sheets

(56) References Cited

OTHER PUBLICATIONS

Asakawa, Nahoko et al., "Pre-vascularization of in vitro three-dimensional tissues created by cell sheet engineering," *Proceedings of the Bioengineering Conference annual meeting of BE D/JSME* (Jan. 2010), vol. 22, p. 24.

Nagase, K. et al., "Temperature-responsive intelligent interfaces for bimolecular separation and cell sheet engineering," *J.R.Soc. Interface* (2009) 6(Supp13), p. S293-309.

Sekiya, Sachiko et al., "Bioengineered cardiac cell sheet grafts have intrinsic angiogenic potential," *Biochem.Biophys.Res.Commun.*, (2006), 34:573-582.

Shimizu, Tatsuya. et al. "Polysurgery of cell sheet grafts overcomes diffusion limits to produce thick, vascularized myocardial tissues," *FASEB J.* (2006) 20:6:708-710 [online Jan. 26, 2006].

Shimizu, Tatsuya et al., "Fabrication of Pulsatile Cardiac Tissue Grafts Using a Novel 3-Dimensional Cell Sheet Manipulation Technique and Temperature-Responsive Cell Culture Surfaces," *Circulation Res.* (2002) vol. 90, p. e40-e48.

Extended European Search Report corresponding to EP 11 82 5225 mailed Feb. 25, 2014, 7 pages.

Extended European Search Report corresponding to EP 11 82 5224 mailed Feb. 25, 2014, 6 pages.

Sakaguchi, Katshisa et al., "In Vitro Engineering of Fascularized Tissue Surrogates," *Scientific Reports* (Feb. 2013) 3(19), 7 pages.

Takei, Takayuki et al., "Fabrication of Endothelialized Tube in Collagen Gel as Starting Point for Self-Developing Capillary-Like Network to Construct Three-Dimensional Organs In Vitro," *Biotechnology and Bioengineering* (Sep. 5, 2009) 95(1):, 7 pages.

Harimoto, Masami et al., "Novel approach for achieving double-layered cell sheets co-culture: overlaying endothelial cell sheets onto monolayer hepatocytes utilizing temperature-responsive culture dishes," *Wiley Periodicals, Inc.* (2002) 464-470.

Kochi, Takashi et al., "Characterization of the Arterial Anatomy of the Murine Hindlimb: Functional Role in the Design and Understanding of Ischemia Models," *PLOS ONE* (Dec. 2013) 8(12): e84047 (10 pages).

* cited by examiner

Femoral artery and vein 3 sheets x 2 times, 6days, 30μL/min 3 sheets x 2 time, 6days, 50μL/min

METHOD FOR MANUFACTURING MULTILAYERED CELL SHEET, MULTILAYERED CELL SHEET HAVING VASCULAR NETWORK OBTAINED THEREBY, AND METHOD OF USE THEREOF

TECHNICAL FIELD

The present invention relates to a method for producing a multilayered cell sheet useful in the field of medicine, biology, drug discovery, pharmacology, etc., a multilayered cell sheet having a vascular network obtained thereby, and a method of use thereof. The present application claims priority to a Japanese application (Japanese Patent Application No. 2010-225200) filed on Sep. 14, 2010.

BACKGROUND ART

Recently, animal cell culture techniques have been remarkably developed, and also research and development related to animal cells have been carried out in a wide variety of fields. In dealing with animal cells of interest, not only the originally developed animal cells per se as well as the products thereof nave been commercialized, but the cells or their cell surface proteins have came to be analyzed to design useful pharmaceuticals, regenerate patient's cells in vitro, or return them after enhancing the function to the patient's body for therapy. At present, the technology of culturing, as well as evaluating, analyzing and using the animal cells are a field that are attracting researchers' attention. Many of the animal cells including human cells are attachment-dependent. Thus, when animal cells are intended to be cultured in vitro, first they must be attached to the surface of a substrate. Sometimes it is necessary to detach the cultured cells, without separating into pieces, while retaining the form as they are cultured on the surface of the substrate.

In particular, with regard to the technology of regenerating the patient's cells in vitro, organ transplantation which intends to replace toe incurable organ with another person's organ has become popular in recent years. Targets include a wide variety of organs such as the skin, the cornea, the kidney, the liver, and the heart, and prognosis after surgery has become extremely well, indicating that the technology is being established as one medical technology. Take corneal transplant as an example. Eye Bank was established in Japan about 50 years ago, along with the start of transplantation activities. However, the number of donors is still small, and while patients who require corneal transplant is about 20,000 in Japan alone, the actual number of patients who can receive the transplantation is said to be one tenth, or about 2000. Despite that corneal transplantation is an mostly established technology, a further improved medical technology is being sought after, due to shortage of donors. Under these circumstances, a technique of culturing the patient's normal cells to the desired size for transplantation was developed.

Japanese Unexamined Patent Publication (Kokai) No. 02-211865 (Patent Document 1) discloses a novel method of culturing cells on a cell culture support, where the surface of the substrate is coated with a polymer having an upper or lower critical solution temperature of 0 to 80° C. in water, the cells are cultured at a temperature not exceeding the upper critical solution temperature or not failing below the lower critical solution temperature, and the cultured cells are detached by increasing or decreasing the temperature of the substrate to exceed the upper critical solution temperature or fall below the lower critical solution temperature, without treatment with an enzyme. Japanese Unexamined Patent Publication (Kokai) No. 05-192138 (Patent Document 2) also describes a method of culturing skin cells using this temperature-responsive cell culture substrate at a temperature not exceeding the upper critical solution temperature or not falling below the lower critical solution temperature end then detaching the cultured skin cells with low damage by increasing or decreasing the temperature of the substrate to exceed the upper critical solution temperature or fall below the lower critical solution temperature. Use of the temperature-responsive cell culture substrate has led to a variety of new developments on known culture techniques. Furthermore, in Japanese Unexamined Patent Re-publication (Saikohyo) No. 02-008387 (Patent Document 3), it was found that by culturing myocardial cells on a cell culture support the surface of which being coated with a temperature-responsive polymer, obtaining a myocardial cell-like sheet, then allowing the cultured multilayered cell sheet to adhere to a polymer membrane at a medium temperature not exceeding the upper critical solution temperature or not failing below the lower critical solution temperature, detaching it as it is together with the polymer membrane, and changing it into a three dimensional structure by a given method, a cell sheet having few structural defects and several functions as a myocardium-like tissue in vitro and a three-dimensional structure can be obtained. However, With the conventional technology described above, the myocardium-like cell sheet cannot be infinitely layered, with about three layers being the limit, and thus there has been a strong need for a technology that easily permits layering for a plurality of times.

In order to resolve the above problems, FASEB. J., 20(6), 708-710 (2006) (Non-patent document 1) attempted to multilayer cell sheets in vivo, and obtained a multilayered myocardial sheet with a thickness of 1 mm. It was found that in order to obtain a thick multilayered cell sheet among them, nutrients and oxygen must be supplied to each multilayered cell and each cell sheet. However, in the method of FASEB. J., 20(6), 708-710 (2006) (Non-patent document 1), cell sheets must be repeatedly transplanted in vivo, and thus the implanted site must be opened each time, which poses a great burden to the recipient of the transplant. Thus, there has been a strong need for a technology that permits simple multilayered for a plurality of times.

CITATION LIST

Patent Documents

Patent Document 1: Japanese Unexamined Patent Publication (Kokai.) No. 02-211865
Patent Document 2: Japanese Unexamined Patent Publication (Kokai) No. 05-192138
Patent Document 3: Japanese Unexamined Patent Re-publication (Saikohyo) No. 02-008387

Non-Patent Documents

Non-patent document 1: FASEB. J., 20(6), 708-710 (2006)

SUMMARY OF THE INVENTION

Technical Problem

As described above, the present invention is intended to solve the problems on layering of cell sheen described above. Thus, the present invention provides a novel method for producing a multilayered cell sheet developed based on a concept entirely different from ode conventional art, a multilayered cell sheet having a vascular network obtained thereby, and a method for using it.

Solution to Problem

In order to solve the above problems, the present inventors have continued research from various viewpoints. As a result, it was found that a vascular network can be constructed in cell sheets and thick cell sheets can be easily layered by producing a vascular bed which includes an artery-vein loop and in which a capillary vascular network is constructed, layering the cell sheets on the vascular bed, and perfusing a culture medium in vitro. It was also found that the effects of drugs on biological tissues can be evaluated in vitro utilizing the multilayered cell sheet with the vascular network obtained thereby. The present invention was made based on such findings.

That is, the present invention is to provide a method for producing multilayered cell sheets, including producing a vascular bed which includes an artery-vein loop and in which a capillary vascular network is constructed; layering cell sheets on the vascular bed; and perfusing a culture medium in vitro to a tissue segment in the living body to construct a vascular network in the cell sheets. Further, the present invention is to provide multilayered cell sheets obtained thereby. Further, the present invention is to provide a method for utilising the multilayered cell sheets. The present invention is considered to be a very important invention achieved only using a cellular structure based on a novel idea, without parallel in the world, that thick multilayered cell sheets can foe produced in vitro utilising the vascular bed. In accordance with the present invention, the multilayered cell sheets may be represented by a cell sheet laminate or a multilayered cell sheet laminate, which each exhibits a laminate obtained by layering a plurality of cell sheets, and no restrictions are imposed by differences in these expressions.

Advantageous Effects of Invention

The production method exhibited in the present invention enables vascular networks to be constructed in cell sheets and enables thick multilayered cell sheets to be easily produced by layering the cell sheets. Such thick multilayered cell sheets are expected to be able to be transplanted as in vivo tissue-like products and to be useful for regenerative medicine for various tissues. In addition, the effects of drugs on biological tissues can be easily evaluated in vitro utilizing the multilayered cell sheets with the vascular network obtained using the vascular bed. Such an evaluation system hot only becomes a substitute for an experimental animal but also provides stable data without depending an individual differences in animals.

DESCRIPTION OF EMBODIMENTS

Figure 1:
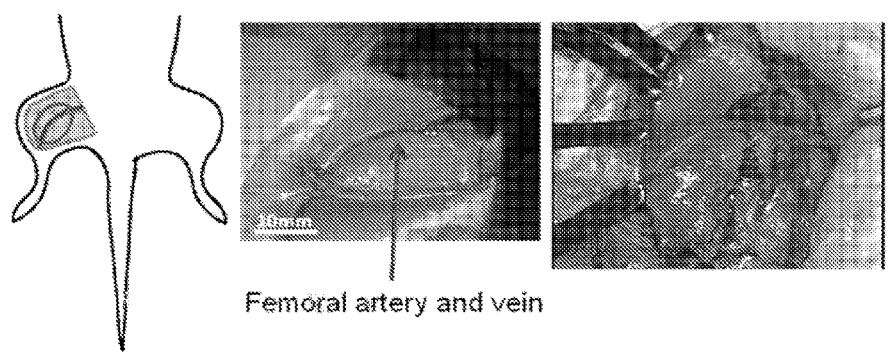
FIG. 1 is a diagram showing the outline of a procedure for fabricating the vascular bed of Example 1.

The purpose of the present invention is to fabricate a thick multilayered cell sheet in a simple manner. For that purpose, it is necessary to construct a vascular network in the multilayered cell sheet as described above. The present invention is characterized by harvesting a biological tissue segment including an artery and a vein into which blood has flowed, perfusing a culture medium in vitro to make a vascular bed, and layering cell sheets on the vascular bed to construct the vascular network in the cell sheets in order to easily construct the vascular network.

A vascular bed refers to a structure, seen in a biological tissue or an organ, in which capillary vessels are combined with tissues in the peripheries thereof. The vascular bed serves the function of exchanging oxygen, glucose, and other nutrients in a biological tissue through the thin wall of capillary vessels innumerably spreading in the vascular bed. A waste product such as carbon dioxide exudes into the capillary vessels of the vascular bed. The reason why tissue fluid is maintained comparatively constant in a biological tissue is because substances are exchanged in capillary vessels. In accordance with the present invention, the vascular bed was utilized for efficiently constructing a capillary vascular network in cell sheets to supply nutrients, oxygen, and the like.

The vascular bed utilized in the present invention may be a biological tissue segment or skin flap including an artery and a vein, into which blood has flowed, or an artificial vascular bed including an artery and a vein, without particular limitation. For example, as the biological tissue segment, the muscle, the mesentery, the greater omentum, or the like, in which a vascular network has been already highly constructed, is convenient. Among them, the muscle, which is a site to which nutrients an a oxygen are sufficiently supplied in view of a biological tissue, that is, in which a vascular network is still more highly constructed, is further convenient. In accordance with the present invention, vascular networks may also be further constructed in these tissue segments, skin flaps, and artificial vascular beds including arteries and veins. Examples of methods therefor include, but are not particularly limited to, a method in which some vessels are closed to further construct a vascular network in a tissue segment or a skin flap, which is subjected to treatment in vivo until blood flow circulation occurs; a method in which the state where the tissue segment or the skin flap is sealed in an aseptic container to connect only the living body, arteries and veins is made in this case and in vivo treatment is performed until a vascular network is further constructed to effect blood flow circulation; a method of administering a cytokine that promotes neovascular formation, such as VEGF or FGF; and the like.

Examples of animal species from which vascular beds used in the present invention are derived include, but are not particularly limited to, human, rat, mouse, guinea pig, marmoset, rabbit, dog, cat, sheep, swine, goat, monkey, chimpanzee, immunodeficient animals thereof, and the like; however, when the multilayered cell sheets according to the present invention are used for therapy on humans, it is more desirable to use vascular beds derived from human, swine, monkey, and chimpanzee.

An artery-vein loop refers to a vessel flow path in which arteries and veins are connected and such a flow path that, when a liquid component such as blood or a culture medium is made to flow into one or a plurality of vessels, the liquid component flows from one or a plurality of vessels except the vessels into which the component is made to flow, is constructed. The length of the artery-vein loop is not particularly limited but is appropriately determined by the size of a vascular bed. As a method of connection between an artery and a vein, which is not particularly limited, a capillary vascular network may be constructed between an artery and a vein or one end of the out artery and one end of the cut vein may also be anastomosed and produced. Examples of methods of constructing a capillary vascular network between an artery an a vein include, but are not also particularly limited to, a method in which a biological tissue segment to which each artery and each vein are connected is cut with an electric knife or the like to make the state of the biological tissue segment to which one artery and one vein are connected, and the segment is placed in the living body for around 1 week while maintaining the state. As a result, a short circuit in capillary vessels (artery-vein loop) occurs between the artery and the vein to construct a flow path from the artery to the vein through the capillary vascular network.

The artificial vascular bed according to the present invention refers to a vascular bed-like structure in which a capillary vascular network is constructed and gel and/or cells are filled in the capillary vascular network. A vascular bed derived from a biological tissue contains various cells derived from the tissue as well as cells that form capillary vessels. Therefore, when the perfusion culture of multilayered cell sheets is performed on the vascular bed derived from the biological tissue, cellular metabolites derived from the vascular bed may also be included in the cell sheet laminate. The included cellular metabolites may be preferred for the maintenance culture of the cell sheets on the vascular bed or may preferably promote the formation of the vascular network in the cell sheets. On the other hand, the included cellular metabolites may adversely affect the maintenance culture depending on the kinds of cells that constitute the cell sheets or may foe unfavorable depending on the application of the multilayered cell sheets (e.g., utilization for transplantation or the case of evaluating the activity of the cell sheets). The vascular bed derived from the living body or the artificial vascular bed may be selected depending on the purpose and the selection is not particularly limited.

Examples of methods of producing artificial vascular beds including arteries and veins include, but are not particularly limited to, a method in which an artery-vein loop in which an artery and a vein in the living body are anastomosed is contained in a region partitioned by the inside of an aseptic container and gel is filled in the partitioned region, which is placed in the living body to construct a capillary vascular network. As the container for producing an artificial vascular bed, which is not particularly limited as long as the container is a biocompatible substrate, materials typical in the field of medical instruments or the like may be used. Specific examples include polyethylene, polypropylene, polystyrene, polyvinyl chloride, nylon, polyurethane, polyurea, polylactic acid, polyglycolic acid, polyvinyl alcohols, polyvinyl acetates, poly(meth)acrylic acid, poly(meth)acrylic acid derivatives, polyacrylonitriles, poly(meth)acrylamide, poly (meth)acrylamide derivatives, polysulfones, polycarbonates, cellulose, cellulose derivatives, polysilicones, glass, ceramic, metals, and the like. These materials may be used singly or in combination. The size of the artificial vascular bed is not particularly limited but cat be appropriately optimised depending on multi-layered cell sheets to be produced, multilayered cell sheets to be transplanted, the site of a biological tissue for producing the artificial vascular bed, and/or the like.

The gel filled in the artificial vascular bed is not particularly limited but gel including a biodegradable polymer is convenient for the purpose of utilizing the obtained multilayered cell sheets for transplantation therapy into the living body. In addition, in that case, the biodegradable polymer unit disappears in vivo to connect the multilayered cell sheets according to the present indention to the living body through vessels. Examples of the kinds of such biodegradable polymers include, but are not particularly limited to, one of collagen, fibrin, gelatine, polysaccharides, elastin, fibronectin, laminin, chitin, chitosan, and the like, or mixtures of two or more kinds.

The gel filled in the artificial vascular bed may be mixed with cells. Examples of the cells with which the gel is mixed include cells that are directly harvested from a biological tissue, cells that are directly harvested and differentiated in a culture system and/or the like, or cell lines, but the kinds thereof are not limited at all. For the purpose of the regeneration of a myocardial tissue or a method for evaluating a myocardial function, examples of cells used include any one or mixtures of two or more cells of myocardial cells, cardiac myoblast cells, myoblasts, mesenchymal stem cells, vascular endothelial cells, endothelial progenitor cells, fibroblasts, bone marrow-derived cells, and adipose-derived cells; and the like, and the kinds thereof are not limited at all. For the purpose of the regeneration of a liver tissue, the production of an artificial liver that simulates a liver tissue, a method for evaluating the function of a liver tissue, or the like, examples of cells used include any one or mixtures of two or more cells of hepatic parenchymal cells, sinusoidal endothelial cells, Kupffer cells, stellate cells, pit cells, biliary epithelial cells, vascular endothelial cells, endothelial progenitor cells, fibroblasts, bone marrow-derived cells, adipose-derived cells, and mesenchymal stem cells; and the like, and the kinds thereof are not limited at all. For the purpose of the regeneration of a kidney tissue, the production of an artificial kidney that simulates a kidney tissue, or a method for evaluating a renal function, examples of cells used include any one or mixtures of two or more cells of renal cells, granule cells, collecting duct epithelial cells, parietal epithelial cells, podocytes, mesangial cells, smooth muscle cells, tubular cells, intercalated cells, glomerulosa cells, vascular endothelial cells, endothelial progenitor cells, fibroblasts, bone marrow-derived cells, adipose-derived cells, and mesenchymal stem cells; and the like, and the kinds thereof are not limited at all. For the purpose of the regeneration of an adrenal tissue, the production of an artificial adrenal gland that simulates the adrenal gland, or a method for evaluating an adrenal function, examples of cells used include any one or mixtures of two or more cells of adrenomsdullary cells, adrenocortical cells, glomerulosa cells, fasciculata cells, reticularis cells, vascular endothelial cells, endothelial progenitor cells, fibroblasts, bone marrow-derived cells, adipose-derived cells, and mesenchymal stem cells; and the like, and the kinds thereof are not limited at all. For the purpose of the regeneration of the skin or a method for evaluating a skin function, examples of cells used include any one or mixtures of two or more cells of epidermal keratinocytes, melanocytes, arrector pili muscle cells, hair follicle cells, vascular endothelial cells, endothelial progenitor cells, fibroblasts, bone marrow-derived cells, adipose-derived cells, and mesenchymal stem cells; and the like, and the kinds thereof are not limited at all. For the purpose of the regeneration of the mucosal tissue or a method for evaluating the function of the mucosal tissue, for example, as cells used, cells harvested from tissues that make up mucosae may be used. Examples of the kinds of the mucosae include buccal mucosa, gastric mucosa, intestinal mucosa, olfactory epithelium, oral mucosa, uterine mucosa, and the like. Mention is made of any one or mixtures of two or more cells of she cells harvested from the mucosal tissues; and the like, and the kinds thereof are not limited at all.

Also, the content ratios of the above-described cells are not particularly limited. In this case, mixing of vascular endothelial cells, endothelial progenitor cells, and/or the like in an artificial vascular bed is convenient since a vascular network is efficiently constructed in the artificial vascular bed.

A vascular network may also be constructed by premixing gel filled in an artificial vascular bed with a vascular growth factor that promotes neovascular formation, and/or the like. Examples of methods of inducing vessels in artificial vascular beds include, but are not also particularly limited, to, a method of directly mixing gel with a vascular growth factor; a method in which FGF which is a vascular growth factor is embedded in microspheres, gel is mixed with the microspheres, and FGF is released from the microspheres for long time; and the like.

As the flow rate of a culture medium perfused in a vascular bed, which is not particularly limited, such a flow rate that a flow path in the vascular bed is not broken may be the maximum flow rate or a flow rate at which the perfused culture medium exudes into the vascular bed and the culture medium can arrive at the surface of the vascular bed may be the minimum flow rate. The numerical value thereof may tot foe specifically exhibited because of being greatly affected by factors such as the size of the flow path, the properties and size of the vascular bed, and the size of a cell sheet.

The present invention is intended to separate a biological tissue segment, a skin flap, or an artificial vascular bed including an artery and a vein, having a vascular network obtained in such a manner, to the outside of the living body, which biological tissue segment, skin flap, or artificial vascular bed is installed in a perfusion culture device in vitro to construct a vascular network in a cell sheet engrafted on a vascular bed. In this case, a material circulated in the vascular bed may be a culture medium, blood, serum, or the like without particular limitation and, as the material that is easily handled, mentions is made of the culture medium. The kind of the culture medium is not particularly limited but may be appropriately selected according to a usual method depending on the kind of a cell to foe cultured and is preferably suitable for cells constituting the cell sheet cultured on the vascular bed. For example, when a cell sheet consisting of myocardial cells is layered on the vascular bed, the M199 medium for culturing myocardial cells may be preferred. The type of the cells to be used in the cell sheet of the present invention is not specifically limited, and cells of the site of interest to be transplanted using the multilayered cell sheet obtained, or cells derived from the desired organ or tissue to be evaluated may be used. For example, when the object is the regeneration of the myocardial tissue or a method for evaluating the myocardial function, cells used include one type or combinations of two types or more of myocardial cells, cardiac myoblasts, myoblasts, mesenchymal stem cells, vascular endothelial cells, vascular endothelial progenitor cells, fibroblasts, bone marrow-derived cells, and adipose-derived cells, and their types are not limited in any way. When the object is the regeneration of the liver tissue, the generation of an artificial liver simulating the liver tissue or a method for evaluating the function of the liver tissue, cells that can be used include, for example, one type or combinations of two types or more of hepatic parenchymal cells, sinusoidal endothelial cells, Kupffer cells, stellate cells, pit cells, biliary epithelial cells, vascular endothelial cells, vascular endothelial progenitor cells, fibroblasts, bone marrow-derived cells, adipose-derived cells, and mesenchymal stem cells, and their types are not limited in any way. When the object is the regeneration of the renal tissue, the generation of an artificial kidney simulating the renal tissue or a method for evaluating the renal function, cells that can be used include, for example, one type or combinations of two types or more of kidney cells, granular cells, collecting duct epithelial cells, parietal epithelial cells, podocytes, mesangial cells, smooth muscle cells, renal tubular cells, interstitial cells, glomerular cells, vascular endothelial cells, vascular endothelial progenitor cells, fibroblasts, bone marrow-derived cells, adipose-derived cells, and mesenchymal stem cells, and their types are not limited in any way. When the object is the regeneration of the adrenal tissue, the generation of an artificial adrenal gland simulating the adrenal gland or a method for evaluating the adrenal function, cells that can be used include, for example, one type or combinations of two types or more of adrenomedullary cells, adrenal cortical cells, spherical layer cells, zonal fasciculate cells, network layer cells, vascular endothelial cells, vascular endothelial progenitor cells, fibroblasts, bone marrow-derived cells, adipose-derived cells, and mesenchymal stem cells, and their types are not limited in any way. When the object is the regeneration of the skin or a method for evaluating the skin function, cells that can be used include, for example, one type or combinations of two types or more of epidermal keratinocytes, melanocytes, piloerection muscle cells, hair follicle cells, vascular endothelial cells, vascular endothelial progenitor cells, fibroblasts, bone marrow-derived cells, adipose-derived cells, and mesenchymal stem cells, and their types are not limited in any way. When the object is the regeneration of the mucosal tissue or a method for evaluating the mucosal tissue function, for example, cells that can be used include buccal mucosa, gastric mucosa, intestinal mucosa, olfactory epithelium, oral mucosa, uterine mucous membrane, and the like. Among the cells harvested from the mucous tissue, one type or combinations of two types or more of the cells can be mentioned, and their types are not limited in any way.

The content ratio of the above cells is not specifically limited. At this time, if the cell sheet contains vascular endothelial cells, vascular endothelial progenitor cells, etc., the vascular network could be conveniently constructed in the cell sheet in an efficient manner.

Cells as used herein include, but not limited to, cells directly harvested from biological tissues, cells directly harvested and differentiated in an culture system, or cell lines. While the origin of these cells is not specifically limited, there can be mentioned, for example, humans, rats, mice, guinea pigs, marmosets, rabbits, dogs, oats, sheep, pigs, goats, monkeys, chimpanzees, or immunodeficient animals thereof. When the multilayered cell sheet of the present invention is used in treating a human subject, cells derived from humans, pigs, monkeys, or chimpanzees may preferably be used.

While cells as used herein are not specifically limited, they may foe cells fluorescently or chromogenically stained using at least one method with a reagent, a protein, a gene, etc.

When reporter gene-introduced cells are used, the activity of a cell sheet or a multilayered cell, sheet can be known by detecting fluorescence derived from a reporter protein obtained by the expression of a reporter gene, or fluorescence emitted by the reaction of a reporter protein and a specific substrate thereof. The reporter gene or reporter protein used include, but not limited to, for example, green fluorescent protein (GFP), chloramphenicol acetyl, transferase (CAT), DsReD, β-glucuronidase, LacZ, Kaede, luciferase, alkaline phosphatase and the like. A method for introducing a gene into the cell may be any conventional method, and include, but not limited to, for example, a lipofection method, a viral vector method, a calcium phosphate method, an electroporation method, a DEAE dextran method, and a microinjection method. Cells derived from a gene-transduced animal (transgenic animal) in which a reporter gene has been introduced into the host's genome using these gene transduction methods may be used. The promoter sequence controlling the expression of the reporter gene is not specifically limited, and may be selected as appropriate depending on the purpose of detecting the expression of the reporter gene.

The cell sheet of the present invention can be obtained by colouring cells at a temperature zone in which the hydration force of a polymer, of which hydration force varies in the temperature range of 0-80° C., is weak on a cell culture support the surface of which is coated with the polymer, and then detaching the cultured cells in a sheet form by varying the temperature of the culture medium to a temperature in which the hydration force of the polymer is strong. At this time, the cells may be cultured at a temperature zone in which the hydration force of a polymer, of which hydration force varies in the temperature range of 0-80° C., is weak on a cell culture support the surface of which is coated with the polymer. Usually, the temperature may preferably be 37° C. which is a temperature for culturing cells. The temperature-responsive polymer for use in the present invention may be any of a homopolymer or copolymer. As such polymers, there can be mentioned polymers described in Japanese Unexamined Patent Publication (Kokai) No. 2-211865. Specifically, it can be obtained by monopolymerization or copolymer station of the following monomers. Monomers that can be used include, for example, a (meth)acrylamide compound, a N-(or N,N-di) alkyl-substituted (meth)acrylamide derivative, or a vinylether derivative, and in the case of a copolymer, any two or more of these can be used. Furthermore, a copolymer with monomers other than the above monomers, a graft polymer or copolymer with each other, or a mixture of polymers and copolymers can be used. Also, crosslinking can foe performed as long as it does not impair the inherent property of the polymer. Since cells are cultured and detached at this time, and separation is carried out in the range of 5° C. to 50° C., temperature-responsive polymers include, but not limited to, poly-N-n-propyl acrylamide (the lower critical dissolution temperature of the monomer alone is 21° C., poly-N-n-propyl methacrylamide (the lower critical dissolution temperature of the monomer alone is 27° C.), poly-N-isopropyl acrylamide (the lower critical dissolution temperature of the monomer alone is 32° C.), poly-N-isopropyl methacrylamide (the lower critical dissolution temperature of the monomer alone is 43° C.), poly-N-cyclopropyl acrylamide (the lower critical dissolution temperature of the monomer alone is 45° C.), poly-N-ethoxyethyl acrylamide (the lower critical dissolution temperature of the monomer alone is 35° C.), poly-N-ethoxyethyl methacrylamide (the lower critical dissolution temperature of the monomer alone is 45° C.), poly-N-tetrahydrofurfuryl acrylamide (the lower critical dissolution temperature of the monomer alone is 28° C.), poly-N-tetrahydrofurfuryl methacrylamide (the lower critical dissolution temperature of the monomer alone is 35° C.), poly-N,N-ethylmethyl acrylamide (the lower critical dissolution temperature of the monomer alone is 56° C.), poly-N,N-diethyl acrylamide (the lower critical dissolution temperature of the monomer alone is 32° C.), and the like. Monomers as used herein for copolymerization include, but not limited to, polyacrylamide, poly-N, N-diethyl, acrylamide, poly-N,N-dimethyl acrylamide, polyethylene oxide, polyacrylic acid and a salt thereof, hydrated polymers such as polyhydroxyethyl methacrylate, polyhydroxyethyl acrylate, polyvinyl alcohol, polyvinyl pyrrolidone, cellulose, and carboxymethyl cellulose.

A method of coating the surface of the substrate with each of the above polymer as used herein include, but not limited to, subjecting the substrate and the above monomer or polymer to an electron beam irradiation (EB), gamma-ray irradiation, ultraviolet ray irradiation, plasma treatment, corona treatment, and an organic polymerization reaction, or physical adsorption such as coating and kneading. The amount coated of a temperature-responsive polymer on the surface of the culture substrate may be in the range or 1.1-2.3 $\mu g/cm^2$, preferably 1.4-1.9 $\mu g/cm^2$, and more preferably 1.5-1.8 $\mu g/cm^2$. If the amount of coating is less than 1.1 $\mu g/cm^2$, the cells on the polymer cannot be easily detached even if stimulated, and inconveniently deteriorates work efficiency. Conversely, if the amount of coating exceeds 2.3 $\mu g/cm^2$, the cells cannot easily attach to the region, and thus the cells cannot be fully attached. In such a case, if a cell-adhering protein is further coated on the temperature-responsive polymer coating layer, the amount of the temperature-responsive polymer coating on the substrate surface may be 2.3 $\mu g/cm^2$ or more, and the amount coated of the temperature-responsive polymer may preferably be 9.0 $\mu g/cm^2$ or less, preferably 8.0 $\mu g/cm^2$ or less, and, suitably 7.0 $\mu g/cm^2$ or less. When the amount coated of the temperature-responsive polymer is 9.0 $\mu g/cm^2$ or more, it makes the attachment of cells difficult, even if a cell-adhering protein is further coated on the temperature-responsive polymer coating layer, and thus is not desirable. The type of such a cell-adhering protein includes, but not limited to, one type or a mixture of two types or more of, for example, collagen, laminin, laminin 5, fibronectin, madrigal, etc. The method for coating these cell-adhering proteins may follow any standard method, and usually a method of applying an aqueous solution of a cell-adhering protein to the substrate surface, and then removing the aqueous solution and rinsing is used. The present invention is a technology of using the cell sheet per se as much as possible using a temperature-responsive culture dish. Thus, an extremely large amount of a cell-adhering protein coated on one temperature-responsive polymer is not preferred. The measurement of the amount coated of a temperature-responsive polymer and the amount coated of a cell-attaching protein may follow any standard method, and there can be mentioned a method of measuring directly the cell-attached part using FT-IR-ATR, and a method of immobilizing a previously labelled polymer in a similar method and then estimating from the amount of the labelled polymer immobilised to the cell-attachment part, and any of the two methods can be used.

According to the method of the present invention, the number of cells inoculated at the time of culturing may vary depending on the animal species used, but may generally be $0.4 \times 10^5$ to $2.5 \times 10^6$ cells/$cm^2$, preferably $0.5 \times 10^6$ to $2.1 \times 10^6$ cells/$cm^2$, and more preferably $0.6 \times 10^6$ to $1.7 \times 10^6$ cells/$cm^2$. When the inoculum concentration is $0.4 \times 10^6$ cell/$cm^2$ or less, generally cells do not grow properly, the function of the cell sheet obtained cannot be expressed, properly, and thus is not preferred in working the present invention. As used herein, in order to detach and recover the cultured cell sheet from the temperature-sensitive substrate, the temperature of the culture substrate to which the cultured cells are attached can be varied to higher than the upper critical dissolution temperature or lower than the lower critical dissolution temperature of the coating polymer on the culture substrate for detaching. At this time, this can foe performed in the culture medium or in another isotonic solution, which can be selected depending on the purpose. In order to detach and recover more quickly and more efficiently, there can be used a method of lightly tapping or shaking the substrate and furthermore a method of stirring the culture medium using a pipet, alone or in combination. The culture conditions other than the temperature may follow any standard method, and is not specifically limited. For example, the medium used may be one to which a known serum such as fetal calf serum (FCS) has been added or a serum-free medium that contains no such serum.

The above will now be explained by taking poly(N-isopropylacrylamide) as an example of a temperature-responsive polymer. Poly(N-isopropylacrylamide) is known to foe a polymer having a lower critical dissolution temperature of 31° C. Therefore, in a free state, the polymer chain dehydrates at a temperature of 31° C. or higher in water, thereby aggregating and becoming cloudy. Conversely, at a temperature of 31° C. or lower, the polymer chain hydrates and becomes dissolved in water. According to the present invention, this polymer has been coated and immobilized on the surface of the substrate such as a petri dish. Thus, at a temperature of 31° C. or higher, the polymer on the substrate surface may dehydrate, but since the polymer chain is coated and immobilised on the substrate surface, the substrate surface comes to exhibit hydrophobicity. Conversely, at a temperature of 31° C. or lower, the polymer on the substrate surface may hydrate, but since the polymer chain is coated and immobilised on the substrate surface, the substrate surface comes to exhibit hydrophilicity. The hydrophobic surface at this time is the surface suitable for cell's attachment and growth, and the hydrophilic surface becomes a surface to which cells cannot attach, and thus the cells in culture or the cell sheen can be easily detached only by cooling.

As a substrate that is coated, those commonly used in cell culture such as glass, reformed glass, polystyrene, a compound such as polymethylmethacrylate may be used, and a substance that can be shaped such as a polymer compound other than the above and ceramics can be used.

The shape of the culture substrate for use in the present invention is not specifically limited, and, for example, a dish, a multiplate, a flask, a cell insert cultured on a porous membrane, or a flat membrane may be mentioned. As a substrate that is coated, those commonly used in cell culture such as glass, reformed glass, polystyrene, a compound such as polymethylmethacrylate, and a substance that can be shaped such as a polymer compound other than the above and ceramics can be used.

The cell sheet for use in the present invention is free of damage by proteolytic enzymes as represented by dispase and trypsin during culture. Thus, the cell sheet detached from the substrate has an adhesive protein, and when the cells are detached in a sheet form, the cell-cell desmosome structure can foe maintained to a certain degree. This permits a favorable adhesion to the vascular bed when placed thereon, and permits an efficient engraftment. For dispase that is a proteolytic enzyme, it is generally known that a cell-cell desmosome structure can be detached while maintaining it for 10-40%. However, since most of the basal membrane-like protein in between the cell-substrate are destroyed, the cell sheet obtained has a weak strength. In contrast, the cell sheet of the present invention maintains 60% or more of both of the desmosome structure and the basal membrane-like protein, and thus various effects mentioned above can be obtained.

A method for fabricating a multilayered cell sheet of the present invention is not specifically limited, and the multilayered cell sheet can be obtained by detaching the cultured cells in a sheet-like form and layering the cultured cell sheets with each other using, as needed, a device for moving cultured cells. At this time, the temperature of the culture medium is not specifically limited, as long as it is lower than the upper critical dissolution temperature when the polymer coated on the surface of the culture substrate has the temperature, or higher than the temperature of the lower critical dissolution temperature when the polymer has the temperature. However, it is needless to say that a low temperature range in which cultured cells cannot grow or a high temperature range in which cultured cells die is obviously not suitable for culturing. Culture conditions other than the temperature may follow any standard method, and is not specifically limited. For example, the medium used may be one to which a known serum such as fetal calf serum (FCS) has been added or a serum-free medium that contains no suet serum. Also, as needed, a device for moving a cell sheet can be used. Such a device is not specifically limited with regard to the material or shape, as long as it can capture the detached cell sheet. As such a material, generally, a material such as polyvinylidene difluoride (PVDF), silicone, polyvinyl alcohol, urethane, cellulose and a derivative thereof, chitin, chitosan, collagen, gelatin, or fibrin glue may be used in the form of a membrane, a porous membrane, an nonwoven fabric, or a woven fabric by being contacted with the cell sheet.

Thus, in accordance with the present invention, a thick multilayered cell sheet can be obtained. When a vascular network as in the present invention was not constructed, three layers were the most in which the multilayered cell sheet could survive. According to the present invention, cell sheets of four layers or more can be layered. At this time, the layering method is not specifically limited, but layering cell sheets of 3 layers or less for a plurality of times may be preferred to layering the cell sheet at one time. Also, the timing of layering may preferably be when a vascular network connected to the vascular bed has been fully constructed. The number of layering times may be appropriately matched with the purpose of use of the multilayered cell sheet, and may preferably be, but not limited to, 5 layers or more, more preferably 10 layers or more, and still more preferably 15 layers or more. When the thickness of the multilayered cell sheet is increased, the effects of the present invention can be markedly received, and a larger amount of cells can be conveniently transplanted to the transplant recipient. In accordance with the present invention, by layering the upper surfaces of two cell sheets with each other, a structure having a channel on both of the upper surface and the lower surface of the multilayered cell sheet can be obtained, and by connecting the channels to a living body, nutrients and oxygen can be efficiently introduced into the multilayered cell sheet.

As a method of promoting construction of a capillary vascular network in the multilayered cell sheet and in between the multilayered cell sheet and the vascular bed, there can be mentioned a method of adding a factor that promotes neovascular formation to a culture medium to be perfused to the vascular bed, or a culture medium for immersing the entire vascular bed, or in both of the culture media. A factor to be added herein may be any factor that induces neovascular formation, and is not specifically limited. There can be mentioned, for example, vascular endothelial growth factor (VEGF), hepatocyte growth factor (HGF), fibroblast growth factor (FGF), epidermal growth factor (EGF), platelet-derived growth factor (PDGF), insulin-like growth factor (IGF), angiopoietin, transforming growth factor-β (TGF-β), placental growth factor (PlGF), MMP, family proteins of the above-mentioned factors, or the like. One or combinations of two or more of the above may be selected as a factor to be added to the culture medium for promoting neovascular formation. The concentration of a neovascular formation-promoting factor to be added to the culture medium may be optimized as appropriate, since it is greatly influenced by a variety of factors such as the type and number of cells included in the cell sheet, the size of the cell sheet, and the type of the vascular bed, and cannot be specifically described herein. As used herein, the terms "culture fluid" and "culture medium" refer to the same meaning.

VEGF is a glycoprotein which is called a vascular endothelial growth factor and binds as a ligand to a vascular endothelial growth factor receptor (VEGFR) generally present on the surface of a vascular endothelial cell. It is known as a factor which stimulates growth, migration, and differentiation, promotes the activity of protease such as plasminogen activator or collagenase and all steps of the formation of a vascular-like structure in collagen gel, so-called neovascular formation, and also promotes neovascular formation in vivo. VEGF has the function of enhancing microvascular permeability and is also involved in monocyte/macrophage activation. In accordance with the present invention, it is added to culture fluid at a concentration of 1 pg/ml, or more which is good, preferably 10 pg/mL or more, most preferably 20 pg/mL or more.

HGF is a factor which is called a hepatocyte growth factor, is generally produced from fibroblasts, macrophages, vascular endothelial cells, vascular smooth muscle cells, and the like, and is characterized mainly by the action, as a paracrine factor, of controlling the growth and functions of epithelial cells. HGF promotes a migration capability and has morphogenetic induction action such as lumen formation, anti-apoptosis action, angiogenic action, immune response regulation action, and the like, not only in hepatic parenchymal cells but also in vascular endothelial cells. In accordance with the present invention, it is added to culture fluid at a concentration of 15 ng/mL or more which is good, preferably 20 ng/mL or more, most preferably 25 ng/mL or more.

FGF is a multifunctional intercellular signal factor which is called a fibroblast growth factor and exhibits various actions such as proliferative activity and differentiation induction on various cells including fibroblasts. Until now, the family consisting of 23 kinds has been formed in human based on structural similarity. Especially, bFGF (basic fibroblast growth factor) is known to be used for coronary angiogenesis therapy by being injected into the ischemia site of the cardiac muscle and is demonstrated to promote the neovaseular formation of the heart. In accordance with the present invention, bFGF is added to culture fluid at a concentration of 10 ng/mL or more which is good, preferably 15 ng/mL or more, most preferably 20 ng/mL or more.

PDGF is a growth factor which is called a platelet-derived growth factor and is involved in regulation such as migration and growth of mesenchymal cells (such as fibroblasts, smooth muscle cells, and glia cells) as well as in growth and neovascular formation of a fetus. It is produced mainly by megakaryocytes or is also contained in platelet α-granules. PDGFs are produced by various cells such as epithelial cells and endothelial cells. PDGFs include at least four kinds of PDGF-A, B, C, and D, where an A-chain and a B-chain have a homodimeric structure or a heterodimeric structure by forming disulfide bonds to provide three isoforms (PDGF-AA, AB, and BB). PDGF-AA, PDGF-AB, and PDGF-BB may also be expressed as FDGF-aa, PDGF-ab, and PDGF-bb, respectively, by those skilled in the art, and any restrictions are not imposed by differences in these expressions. In accordance with the present invention, PDGF-BB is added to culture fluid at a concentration of 4 ng/mL or more which is good, preferably 5 ng/mL or more, most preferably 7 ng/mL or more.

IGF is a polypeptide which is called an insulin-like growth factor and has a sequence that is highly similar to that of insulin. IGF-2 is considered to be the first growth factor needed by initial development while the expression of IGF-1 is seen in a later stage. The insulin-like growth factor 1 (IGF-1) is secreted mainly in the liver as a result of stimulation with growth hormone (GH). Host cells of the human body, particularly muscle, bone, liver, kidney, nerve, skin and lung cells, are affected by IGF-1. Neovascular formation is also known to be promoted by IGF-1. In accordance with the present invention, IGF-1 is added to culture fluid at a concentration of 600 ng/mL or more which is good, preferably 800 ng/mL or more, most preferably 1000 ng/mL or more.

A multilayered cell sheet obtained according to the present invention can be transplanted to a given site of a living body. The method includes, but not particularly limited to, a method of connecting a channel provided in the multilayered cell sheet of the present invention and the blood vessel of a living body and a method of allowing the surface of a multilayered cell sheet to attach to a living body, whereupon blood vessel induction may have been carried out in advance at the transplanted sits, and is not specifically limited. As used herein, a method of inducing blood vessels includes, but not limited to, for example, a method of embedding FGF, a blood vessel growth factor, into microspheres, and allowing it to set on a living body for 8-10 days while varying the composition, size, and injection range of the microspheres, a method of cutting a polyethylene terephthalate mesh into an arbitrary sire, preparing a bag-like product, placing FGF dissolved in a high concentration agarose solution in the bag, and removing the bag 8-10 days later to fabricate a space in which blood vessels were induced, and the like.

By utilizing a cell sheet laminate according to the present invention in a human, the functions of the transplanted cell sheet lam irate are expressed in the living body of the human for a long period. In addition, the expression levels of the functions can be controlled by either or both of the size and shape of the detached cell sheet laminate. Such a cell sheet laminate may be used for the purpose of therapy for a disease, or each disease with a disorder selected from the group consisting of cardiac failure, ischemic heart disease, myocardial infarction, cardiomyopathy, myocarditis, hypertrophic cardiomyopathy, dilated phase of hypertrophic cardiomyopathy, and dilated cardiomyopathy, for example, when constituting cells that constitute the cell sheet are cells constituting a heart tissue, such as myocardial cells, cardiac myoblast cells, myoblasts, or mesenchymal seem cells. In addition, for example, in the case of cells constituting a liver tissue, such as hepatic parenchymal cells, sinusoidal endothelial cells, Kupffer cells, stellate cells, pit cells, biliary epithelial cells, or mesenchymal stem cells, it may be used for the purpose of therapy for patients with hepatic enzyme coloboma, hemophilia, coagulation defect, hepatic failure, fulminant hepatitis, hepatic cirrhosis, and hepatectomy, therapy for infections and the like, or aid of liver functions. In addition, for example, in the case of cells constituting a kidney tissue, such as renal, cells, granule cells, collecting duct epithelial cells, parietal epithelial cells, podocytes, mesangial cells, smooth muscle cells, tubular cells, intercalated cells, or glomerulosa cells, it may be used for the purpose of therapy for renal dysfunction, renal failure, and glomerulonephritis, therapy for infections and the like, or aid of renal functions. In addition, for example, when cells used are cells constituting an adrenal tissue, such as adrenomedullary cells, adrenocortical cells, glomerulosa cells, fasciculate cells, or reticularis cells, it may be used for the purpose of therapy for adrenocortical insufficiency, hypoadrenocorticism, Cushing's syndrome, aldosteronism, adrenal hypoplasia, and adrenal enzymatic defect, therapy for infections and the like, or aid of adrenal functions. In addition, for example, cells used are cells constituting an epidermal, tissue, such as epidermal keratinocytes, melanocytes, arrector pili, muscle cells, or hair follicle cells, it may be used for the purpose of skin transplantation or hair transplantation. In addition, for example, in the case of cells constituting mucosa, harvested from a tissue such as buccal mucosa, gastric mucosa, intestinal mucosa, olfactory epithelium, oral mucosa, uterine mucosa, or the like, it can be used for the purpose of therapy for endermosis or therapy for infections. A transplantation site is appropriately specified depending on a cell type used and these are not particularly limited.

Utilization of the multilayered cell sheets that are layered on the vascular bed according to the present invention enables the evaluation of the effect of a drug. There can be evaluated the effect of a drug or the like used for the purpose of therapy for a disease, or each disease with a disorder selected from the group consisting of cardiac failure, ischemic heart disease, myocardial infarction, cardiomyopathy, myocarditis, hypertrophic cardiomyopathy, dilated phase of hypertrophic cardiomyopathy, and dilated cardiomyopathy, for example, when cells constituting the cell sheets that are layered on the vascular bed are cells constituting a heart tissue, such as myocardial cells, cardiac myoblast cells, myoblasts, or mesenchymal stem cells. In addition, there can be evaluated a drug or the like which can be used for the purpose of therapy for patients with hepatic enzyme coloboma, hemophilia, coagulation defect, hepatic failure, fulminant hepatitis, hepatic cirrhosis, and hepatectomy, or therapy for infections and the like, for example, in the case of cells constituting a liver tissue, such as hepatic parenchymal cells, sinusoidal endothelial cells, Kupffer cells, stellate cells, pit cells, biliary epithelial cells, or mesenchymal stem cells. In addition, there can be evaluated a drug or the like which can be used for the purpose of therapy for renal dysfunction, renal failure, and glomerulonephritis, or therapy for infections and the like, for example, in the case of cells constituting a kidney tissue, such as renal cells, granule cells, collecting duet epithelial cells, parietal epithelial cells, podocytes, mesangial cells, smooth muscle cells, tubular cells, intercalated cells, or glomerulosa cells. In addition, there can be evaluated a drug or the like which can foe used for the purpose of therapy for adrenocortical insufficiency, hypoadrenocorticism, Cushing's syndrome, aldosteronism, adrenal hypoplasia, and adrenal enzymatic defect, or therapy for infections and the like, for example, when cells used are cells constituting an adrenal tissue, such as adrenomedullary cells, adrenocortical cells, glomerulosa cells, fasciculata cells, or reticularis cells. In addition, there can be evaluated a drug or the like which can be used for the purpose of skin transplantation, hair transplantation, or hair regeneration, for example, cells used are cells constituting a skin tissue, such as epidermal keratinocytes, melanocytes, arrector pili muscle cells, or hair follicle cells. In addition, there can be evaluated a drug or the like which can foe used for the purpose of therapy for endermosis, or infections, for example, in the case of cells constituting mucosa, harvested from a tissue such as buccal mucosa, gastric mucosa, intestinal mucosa, olfactory epithelium, oral, mucosa, uterine mucosa, or the like.

Examples of methods for evaluating a drug or the like in vitro by utilizing the multilayered cell sheets which are layered on the vascular bed according to the present invention include, but are not particularly limited to, a method for detecting the expression of a reporter gene introduced info cells that make up the multilayered cell sheets. The reporter gene is not particularly limited but mentions are made of, for example, utilisation of cells that constantly express a luciferase gene as the reporter gene. Light can be emitted by adding luciferin, which is a substrate for a luciferase protein, to a perfused culture medium. The amount of a substrate flowing into a cell sheet is proportional to the amount of a capillary vascular network constructed in the cell sheet. The construction degrees of capillary vascular networks in cell sheets can be compared by measuring fluorescence intensity. In addition, light emitted by a luciferase protein also varies in proportion to intracellular ATP content. In other words, cellular metabolisms can be compared by comparing the amounts of emitted light. By perfusing a culture medium added with an optional drug or the like to multilayered cell sheets on a vascular bed and then perfusing a substrate, the effect of the drug on the multilayered cell sheets can also be evaluated utilizing this principle. Evaluation of a drug or the like on cellular metabolism can be carried out by a variation in the detected amount of emitted light. In addition, by performing the perfusion culture of a culture medium added with an optional drug and then detecting cytokines, other proteins, and cellular metabolites that are eluted into the culture medium, the effect of the drug or the like on multilayered cell sheets can be evaluated and electrical signals generated by a cell can be detected.

Use of a method for evaluating a drug or the like in vitro by utilizing the multilayered cell sheets layered on the vascular bed according to the present invention also enables in vitro evaluation of the effect of a drug or the like, which has not been able to be evaluated until now unless administered to an animal or a human. In addition, the drug effect can be stably and easily evaluated with hardly affected by another tissue since the multilayered cell sheets which simulate an optional tissue is utilized. The present invention is expected to be utilized for development of a novel drug or the like.

If the cell sheet or the multilayered cell sheet of the present invention can be transplanted to animals, they would be animals for evaluating pharmaceuticals. And the amount expressed of function can be controlled in the size and shape of the detached multilayered cell sheet. Animals used herein include, but not limited to, rats, mice, guinea pigs, marmosets, rabbits, dogs, pigs, chimpanzees, or immunodeficient animals thereof. For example, such animals may be used in, but not limited to, a system for evaluating cardiac function in which a test substance can be administered to these animals to judge the effect of the test substance on the cardiac function.

EXAMPLES

While the present invention will now be explained in detail with reference to specific examples, it should be noted that the present invention is not limited to them in any way.

Example 1

Figure 2:
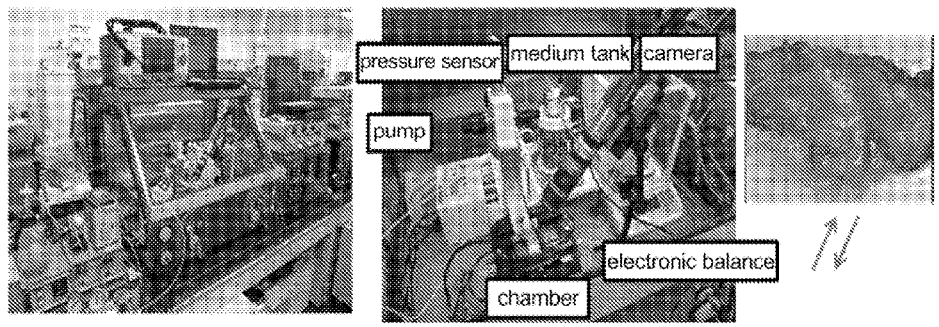
FIG. 2 is a diagram showing the state of the perfusion of a culture medium to the vascular bed obtained in Example 1.

In order to promote neovascular formation into transplanted and layered myocardial tissues, the epidermis of the femoral region of a rat was incised, a quadriceps skeletal muscle tissue containing the femoral artery and vein was cut in 1.5 cm×2.0 cm per side with an electric knife to make the state in which only the femoral artery and vein were connected to the quadriceps skeletal muscle tissue of 1.5 cm×2.0 cm per side, and only the incised epidermis was sutured while maintaining the state. Short circuit in capillary vessels (artery-vein loop) was caused by placing the quadriceps skeletal muscle tissue cut in 1.5 cm×2.0 cm per side in the living body for 1 week to produce an organ-like vascular bed having a vascular network from the artery to the vein (FIG. 1). The vascular bed in which the artery-vein loop was generated was completely cut from the femoral region of the rat, each of the femoral artery and the femoral vein was connected to a tube through which a culture, medium was perfused, and a tissue perfusion bioreactor capable of circulating the culture medium into the vascular bed was produced (FIG. 2).

In parallel with the production of the vascular bed bioreactor, myocardial cell sheets were produced. As the myocardial cells, myocardial cells isolated from the heart of a 0-day-old SD rat and cultured, were used. After the extraction of the heart from the postnatal rat, the myocardial cells were isolated using collagenase type II (manufactured by Worthington Corporation) which is an enzyme decomposing collagen, which is the major component of the tissue. The isolated myocardial cells were seeded, in a temperature-responsive culture dish (having a diameter of 35 mm, Dish Upcell Type-G (manufactured by CellSeed Inc.)) at a concentration of $320 \times 10^4$ cells/dish. After 4 days, sheet-like myocardial cell groups were collected by decreasing temperature to 20° C. when the myocardial cells became in the continent state on the surface of the culture dish. When three of these sheets were layered and transplanted as myocardial cell sheets on the vascular bed connected to the bioreactor, multilayered cell sheets were able to be cultured on the vascular bed (FIG. 2). (Search for Method for Maturing Capillary Vascular Network in Multilayered Cell Sheets in Vascular Bed and on Vascular Bed):

In order to search for cytokines promoting neovascular formation, contained in rat serum, the hearts of rats were punctured to collect blood, and detection thereof was attempted by an ELISA assay (n=3). As a result, 16 pg/mL of bFGF was confirmed to exist in the rat serum (FIG. 4A). Thus, it was decided to add bFGF to a culture medium to be perfused by a tissue perfusion bioreactor.

Figure 3:
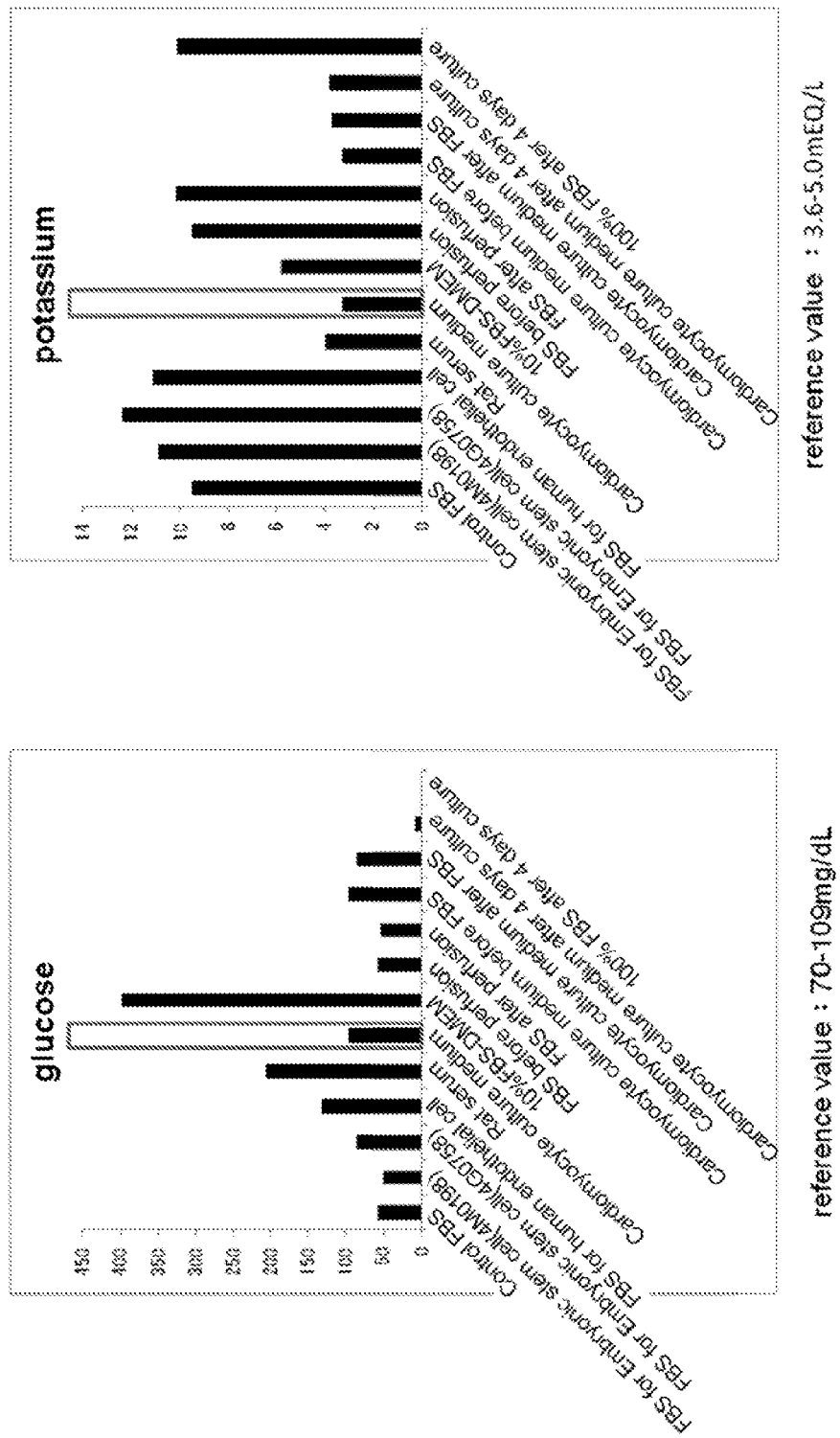
FIG. 3 is a diagram showing the outline of the culture medium circulated to the vascular bed used in Example 1.
Figure 4:
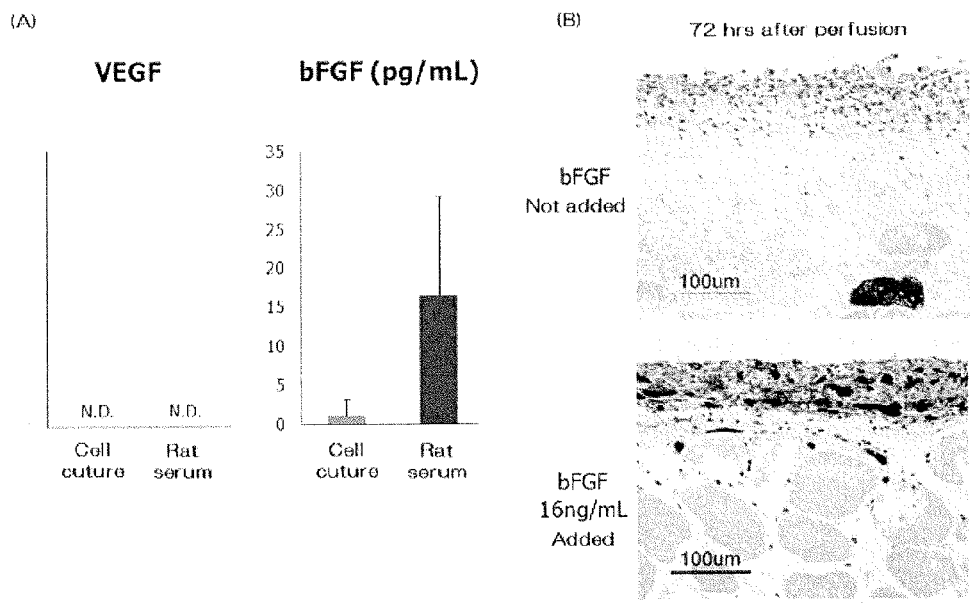
FIG. 4 is a diagram showing the state of a vascular network in multilayered cell sheets of Example 1.

Culture fluid for myocardial cells, added with bFGF at 16 ng/mL, which was 1000 times greater than the concentration of bFGF existing in serum, was selected as perfusate to carry out culture (FIGS. 3 and 4). Multilayered cell sheets were transplanted on a vascular bed and cultured for 72 hours, followed by making India ink, instead of the culture medium, flow back, and confirming a region stained black to confirm neovascular formation, and a lumen stricture (FIG. 4B); and, as a result, regions stained black were observed widely in the vascular bed and in the multilayered cell sheets in the cell sheets added with bFGF and cultured, in comparison with the multilayered cell sheets subjected to perfusion culture without adding bFGF. The results revealed chat a capillary vascular network with lumen formation was constructed in the vascular bed and the multilayered cell sheets when bFGF was added to the culture medium (FIG. 4B).

Figure 5:
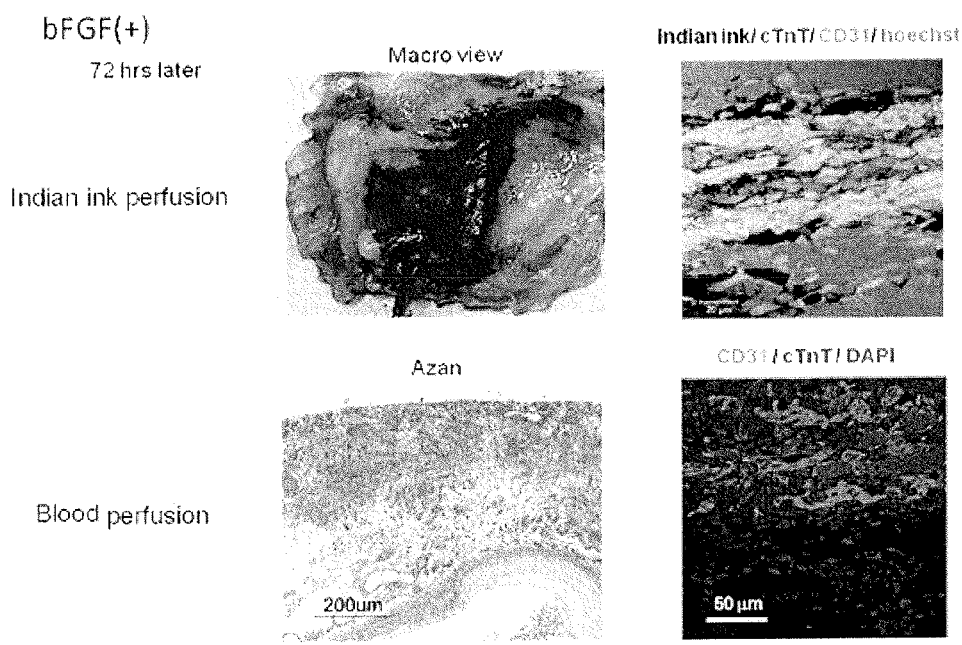
FIG. 5 is a diagram showing the state of a vascular network in multilayered cell sheets of Example 1.

India ink or blood was perfused at a flow rate of 30 μL/min using a tissue perfusion bioreactor in order to confirm in detail whether connection between a myocardial cell sheet and a vascular bed through capillary vessels was also formed. As a result, a part of the myocardial cell sheet transplanted on the vascular bed was strongly stained (FIG. 5) with Indian ink (upper section in FIG. 5) or blood (lower section in FIG. 5). The observation of tissue segments stained with H, E and Azan also revealed that Indian ink flowed into a myocardial cell sheet on a vascular bed (FIG. 5). Further, immunohistostaining using CD31 and a cardiac troponin T antibody revealed that vascular endothelial cells formed a tubular structure in a peripheral area into which Indian ink or red blood cells flowed and that nutrients and oxygen were supplied through vessels (FIG. 5). In other words, if was revealed that vessels were able to be induced into a myocardial cell sheet even under in vitro conditions even if in vivo layering of cell sheets as attempted in FASEB. J., 20(6), 708-710 (2006) (Hon Patent Literature 1) was not performed.

Example 2

Figure 6:
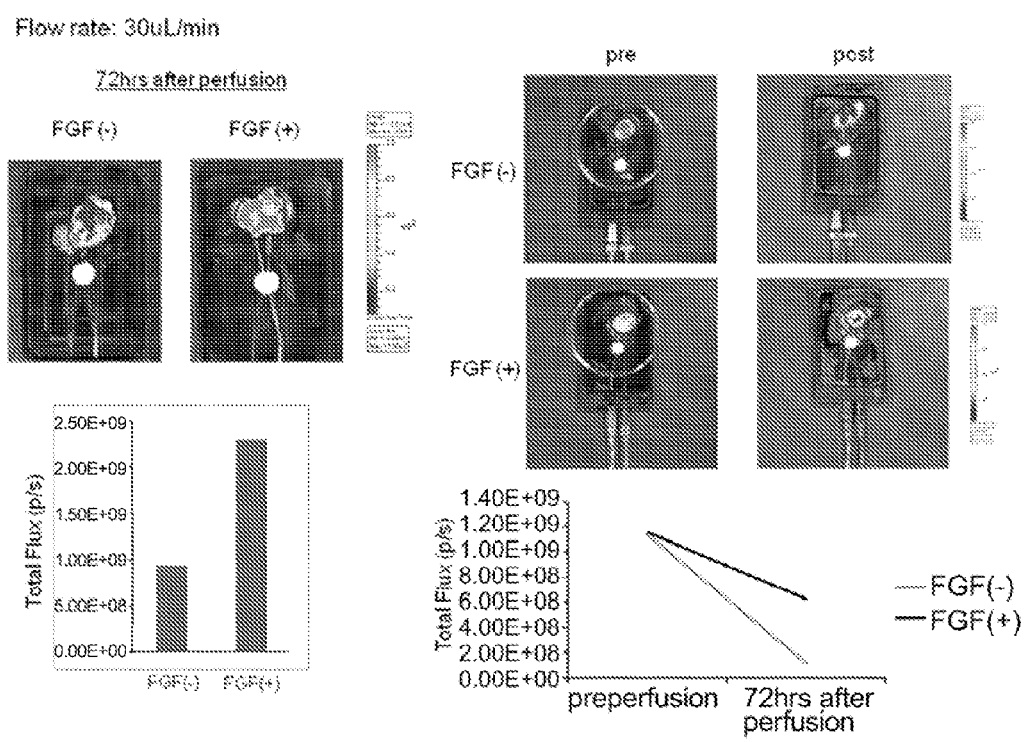
FIG. 6 is a diagram showing the activity of multilayered cell sheets of Example 2.

Method for Measuring Drug Effect Utilizing Myocardial Cell Sheet Laminate on Vascular Bed In cell sheets layered on a vascular bed, cells isolated, from the heart of a 0-day-old transgenic rat into which a luciferase gene was introduced were used. The cell sheets were layered on the vascular bed by the same method as in Example 1, perfusion culture was performed with or without addition of FGF (16 ng/mL), a culture medium containing luciferin which was a substrate for a luciferase protein was perfused instead of the culture medium after 72 hours, and fluorescence intensity was measured by an image analyzer (FIG. 6). The fluorescence intensity is expressed by pseudo color and warmer color exhibits higher fluorescence intensity (FIGS. 6A and C). Fluorescing occurs depending on the substrate and ATP concentration and greater fluorescence exhibits higher cellular activity. FIGS. 6B and D are the graphs of the fluorescence intensity. There was a tendency to make the fluorescence intensity higher by perfusion culture with addition of FGF than perfusion culture without the addition thereof. Therefore, it was revealed that a matured vascular network was induced, the amount of the culture medium flowing into the cell sheets was increased, and higher cellular activity was exhibited in the multilayered cell sheets subjected to the perfusion culture with the addition of FGF compared with the case of the perfusion culture without the addition thereof.

The evaluation of a drug on layered myocardial cell sheets was attempted using a luciferase imaging method. The intensity of fluorescence with luciferase depends on cellular activity and the concentration of luciferin flowing into cell sheets, as mentioned above. In the myocardial layered sheets, capillary vessels in the multilayered cell sheets contract and relax according to beating since the beating is also maintained on the vascular bed. Therefore, the amount of a perfused culture medium is temporarily decreased during the contraction. As a result of the observation of the fluorescence intensity over time by the luciferase imaging method, it was revealed that the fluorescence intensity was increased and decreased. The effect of a drug affecting myocardial cells was measured utilising such a finding. As the drug, a β-blocker was used. The β-blocker is a drug that exhibits a blocking action only on a β-receptor among the adrenergic receptors of sympathetic nerves and is clinically used in antihypertensive drugs and for prevention of the anginal symptoms of labor stenocardia patients, arrhythmia (atrial fibrillation, sinus tachycardia, lower heart rate during premature contraction), improvement in the cardiac functions of patients with cardiac failure, sudden death thereof, and circulatory diseases such as myocardial infarction. Culture was performed for 72 hours, as a perfusion culture medium for multilayered cell sheets produced by the method described in Example 1, using the perfusion culture medium to which the β-blocker was added and a culture medium without addition thereof. Then, a culture medium to which luciferin was added was perfused to observe a variation in fluorescence intensity over time by the luciferase imaging method. As a result, the beating power, the number of times of light emission, and light emission interval of the myocardial cell sheets to which the control drug was added were hardly affected whereas reduction in fluorescence intensity, reduction in the number of times of light emission, and delay of a light emission interval occurred in the layered myocardial cell sheets subjected to the perfusion culture with the culture medium to which the β-blocker was added. Therefore, it was revealed that the present invention enables the easy and quantitative in vitro evaluation of the influence of a drug affecting myocardial functions by utilizing the layered myocardial cell sheets.

Example 3

Search for Method for Thickening Myocardial Cell Sheet

Figure 7:
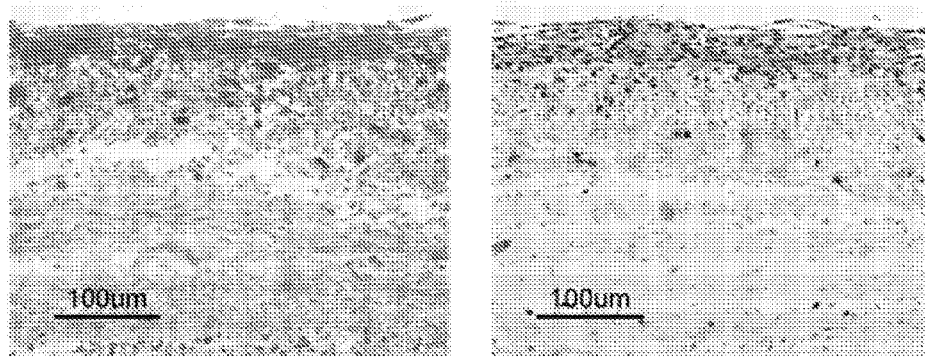
FIG. 7 is a diagram showing the state of multilayered cell sheets of Example 3, which are further stacked.
Figure 7:
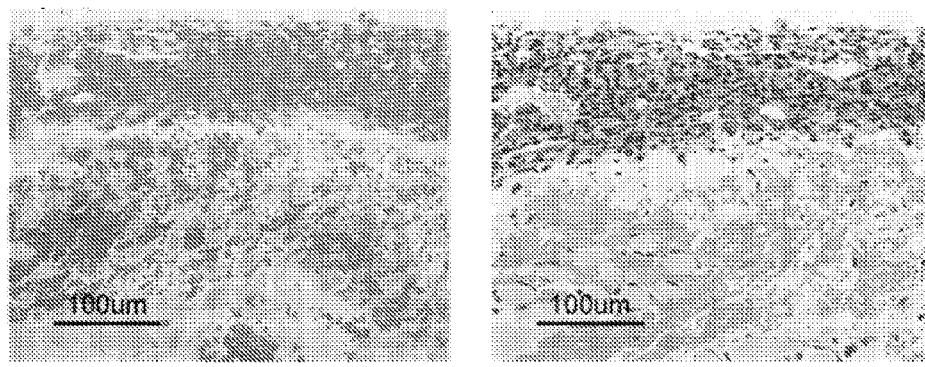

Three myocardial cell sheets were further engrafted on the cell sheet layer, in which the obtained vascular network was constructed, and were further cultured for 6 days. As a result, it was found that the later mounted cell sheets survived at both perfusate rates of 30 μL/min and 50 μL/min and vascular networks were constructed in the cell sheets (FIG. 7). However, since a first layered region was weakly stained in the cell sheets subjected to the perfusion culture at 30 μL/min while both first and second layered regions with the perfusion culture at 50 μL/min were more strongly stained, it was revealed that it is preferable to increase the flow rate of perfusate in order to construct thick multilayered cell sheets. Based on these results, a procedure for constructing a capillary vascular network in myocardial layered sheets was able to be established by utilizing the vascular bed as a field for neovascular formation.

Example 4

Search for Cytokine Promoting Neovascular Formation in Multilayered Cell Sheets

Example 1 revealed that the capillary formation in the myocardial cell sheets and between the vascular bed and the cell sheets was promoted by adding bFGF to the culture fluid to foe perfused in the method for layering cell sheets by the perfusion bioreactor utilizing the vascular bed. In Example 1, the method of puncture into the heart was used as the method of collecting blood from the rats. Therefore, there can foe considered the possibility that the addition of stimulation due to the puncture induced inflammatory response and/or the like and affected blood cytokine concentration. Thus, a decapitation blood collection method was adopted as a blood collection method inducing less stimulation and blood was collected.

Figure 8:
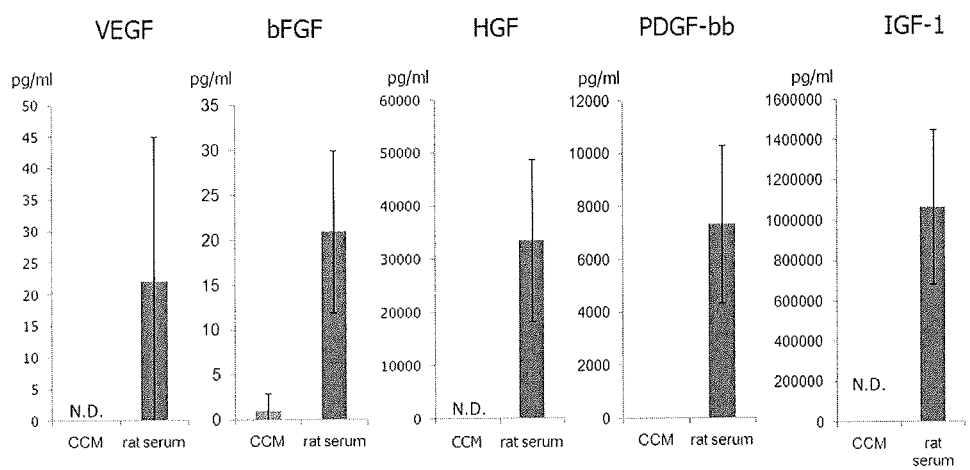
FIG. 8 is a diagram showing the results of searching cytokines that promote neovascular formation in multilayered cell sheets of Example 4. Blood was harvested from rats and the concentrations of cytokines contained in serum were measured by an ELISA assay.

The concentrations of cytokines contained in serum and involved in promotion of angioplasty were measured by an ELISA assay (FIG. 8). As a result, it was revealed that VEGF (22±23 pg/ml) as well as bFGF (21±9 pg/ml), HGF (33500±15218 pg/ml), PDGF-bb (7345±2976 pg/ml), and IGF-1 (1065565±384348 pg/ml), which had not been able to foe detected by the cardiopuncture method and were involved in neovascular formation, were contained, and it was estimated that these cytokines constantly promoted the neovascular formation.

Thus, myocardial cell sheets were transplanted on a vascular bed as in the case of Example 1 and perfusion culture was performed at a flow rate of 50 μL/min for 72 hours using myocardial cell culture fluid containing or not containing 22 pg/ml of VEGF, 21 pg/ml of bFGF, 33500 pg/ml of HGF, 7345 pg/ml of PDGF-bb, or 1065565 pg/ml of IGF-1 in each amount using the tissue perfusion bioreactor illustrated in FIG. 2. As a result, it was revealed that capillary formation was promoted in the cell sheets and between the vascular bed and the cell sheets when perfusion culture was performed with the culture fluid added with each of VEGF, bFGF, HGF, PDGF-bb, and IGF-1, compared with the culture fluid added with no cytokine.

Example 5

Figure 9:
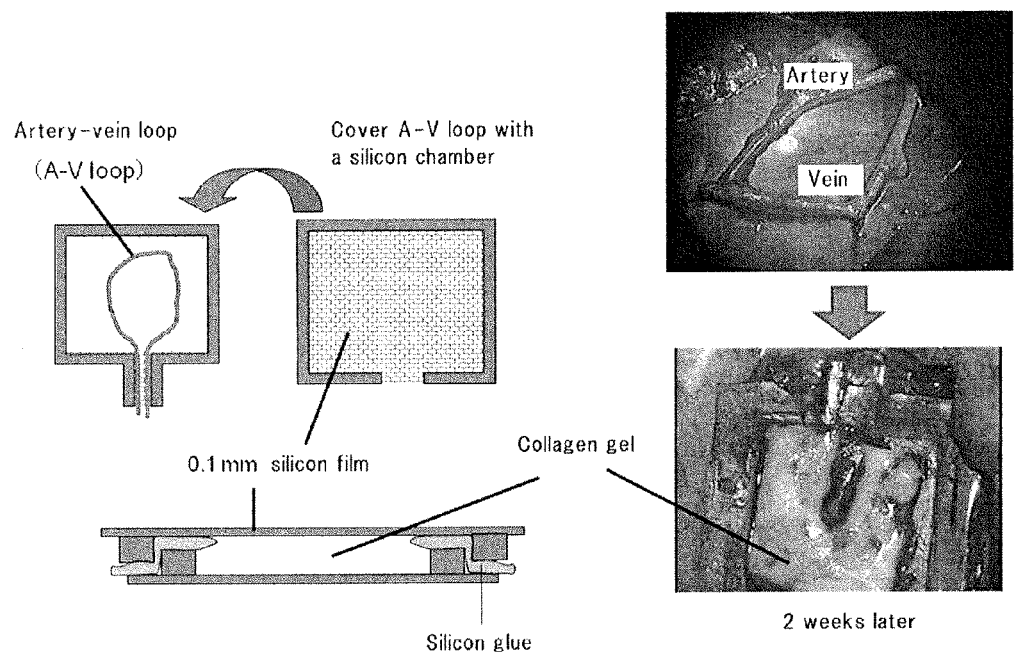
FIG. 9 is a diagram showing the outline of a procedure for fabricating the vascular bed of Example 5.

Artificial Vascular Bed in which Artery-Vein Loop is Formed in Silicon Chamber, and Method for Producing Multilayered Cell Sheets Utilizing the Artificial Vascular Bed As a vascular bed for producing multilayered cell sheets in vitro, an artificial vascular bed utilising a silicon chamber was produced (FIG. 9).

Figure 10:
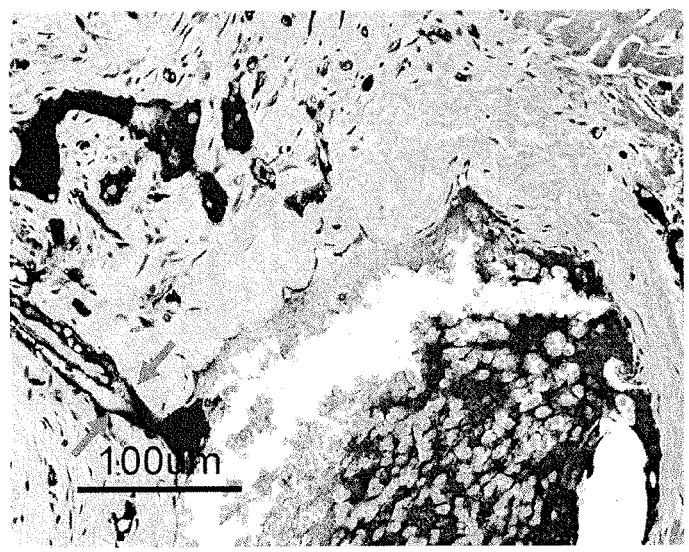
FIG. 10 is a diagram showing capillary vessels newly formed in the vascular bed fabricated in Example 4. In a region sandwiched between arrows, there are newly-generated capillary vessels.

The epidermis of a rat was incised to detach only the femoral artery and the femoral vein from a biological tissue. The femoral artery and the femoral vein were cut and the cut areas of the femoral artery and the femoral vein were anastomosed to each other to produce an artery-vein loop (A-V loop). The artery-vein loop produced by anastomosing the artery and the vein in the living body was inserted info a silicon chamber covered with a silicon film of 0.1 mm in thickness, which was a container, made of silicon, of 1.5 cm in height, 1.5 cm in width, and 3 mm in thickness, and the periphery thereof was filled with a mixture of 2% atelocollagen, $10^6$ vascular endothelial cells, and fibroblasts. Then, the incised epidermis was sutured to place the silicon chamber containing the artery-vein loop in the living body for 2 weeks (FIG. 9). As a result, a capillary vascular network was newly generated from the artery-vein loop in the silicon chamber (FIG. 10). FIG. 10 illustrates a tissue segment in which India ink was perfused instead of culture fluid from the artery side of the vascular bed produced utilising the silicon chamber. Black regions indicate vessel regions. The region sandwiched between the arrows indicates a vessel newly generated from the vein portion.

After 2 weeks, the femoral region of the rat was incised again, the femoral artery and femoral vein connected info the silicon chamber were cut, and the artificial vascular bed produced in the silicon chamber was cut from the living body. One side, covered with a thickness of 0.1 mm, of the silicon chamber, was removed, and, instead of the vascular bed including the biological tissue segment illustrated in FIG. 2, the femoral artery and femoral vein connected into the silicon chamber were connected to the tube, through which the culture medium was circulated, of the bioreactor. Cell sheets were layered on the artificial vascular bed produced in the silicon chamber and were subjected to perfusion culture in the same manner as in Example 1. As a result, capillary vessels were formed in the cell sheets and between the vascular bed and the cell sheets, as in the case of the multilayered cell sheets produced by utilizing the vascular bed of the biological tissue, and thick multilayered cell sheets were able to be produced.

Example 6

Figure 11:
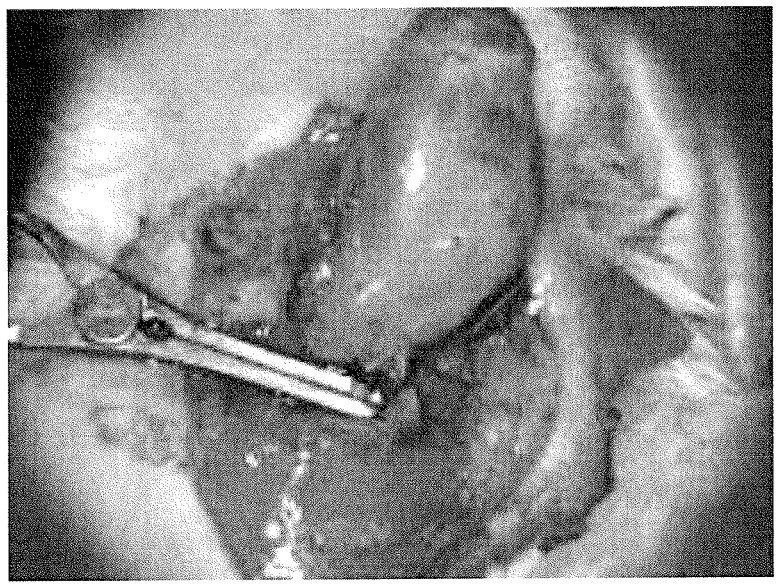
FIG. 11 is a diagram of re-transplantation into the living body for confirming the function of the multilayered cell sheets fabricated in Example 4.

Retransplantation into Living Body for Confirming Functions of Multilayered Cell Sheets Whether the layered myocardial cell sheets produced by utilizing the vascular bed were functional even when transplanted was confirmed by retransplanting the layered myocardial cell sheets into a rat (FIG. 11).

The left femoral artery connected to the vascular bed, on which the myocardial cell sheets were layered, produced in Example 1, was anastomosed to the left internal carotid artery while the left femoral vein of the vascular bed was anastomosed to the left external jugular vein. As a result, it was confirmed that blood also normally flowed into the multilayered cell sheets. It was also confirmed that the beating of the myocardial cell sheets was maintained and that the multilayered cell sheets produced by the method had maintained functions even in the case of the transplantation.

INDUSTRIAL APPLICABILITY

The production method exhibited in accordance with the present invention enables vascular networks to be constructed in cell sheets and enables thick multilayered cell sheets to be easily produced by layering the cell sheets. Such thick multilayered cell sheets are useful as in vivo tissue-life products for regenerative medicine for various tissues as well as for evaluation of the effects of drugs for the purpose of therapy.

In accordance with the production method of the present invention, a vascular network can be constructed in a cell sheet, and by layering the sheet, a thick multilayered cell sheet can be easily fabricated. Such a thick multilayered cell sheet is useful as an in-vivo tissue substitute in regenerative medicine for various tissues as well as for evaluation of the effects of drugs for the purpose of therapy.

What is claimed is:

1. A multilayered cell sheet product comprising a vascular bed, multiple layers of cell sheets layered on the vascular bed, and a capillary vascular network in the cell sheets,
   wherein the vascular bed comprises a biological tissue with a femoral artery-vein loop and circulating culture medium, and
   wherein the capillary vascular network is generated by layering the cell sheets on the vascular bed and perfusing the culture medium in vitro into the vascular bed to induce the capillary vascular network into the cell sheets.

2. The multilayered cell sheet product according to claim 1, wherein the biological tissue is derived from a muscle.

3. The multilayered cell sheet product according to any one of claim 1, or 2, wherein the culture medium comprises a cytokine involved in promotion of neovascular formation.

4. The multilayered cell sheet product according to claim 1, wherein each cell sheet was obtained by culturing cells on a coating polymer at a temperature which is lower than the upper critical dissolution temperature of the coating polymer or higher than the lower critical dissolution temperature of the coating polymer, and then detaching the cultured cells in a sheet at a temperature which is higher than the upper critical dissolution temperature of the coating polymer or lower than the lower critical dissolution temperature of the coating polymer.

5. The multilayered cell sheet product according to claim 4, wherein the polymer, of which hydration force varies in the temperature range of 0-80° C., is poly(N-isopropylacrylamide).

6. The multilayered cell sheet product according to claim 5, wherein the number of layers of cell sheets is four or more.

7. The multilayered cell sheet product according to claim 1, wherein the cell sheets are derived from a tissue selected from heart tissue, liver tissue, kidney tissue, adrenal tissue, skin tissue, or mucosal tissue.

8. The multilayered cell sheet product according to claim 7, containing vascular endothelial cells.

9. The multilayered cell sheet product according to claim 7, wherein the cell sheets comprise one or more types of cells from the tissue.

* * * * *